US009149288B2

(12) United States Patent
Teague et al.

(10) Patent No.: US 9,149,288 B2
(45) Date of Patent: Oct. 6, 2015

(54) MEDICAL RETRIEVAL DEVICE

(75) Inventors: James A. Teague, Spencer, IN (US); Juli Curtis, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 279 days.

(21) Appl. No.: 12/890,848

(22) Filed: Sep. 27, 2010

(65) Prior Publication Data

US 2011/0066159 A1    Mar. 17, 2011

Related U.S. Application Data

(63) Continuation of application No. 10/958,563, filed on Oct. 6, 2004, now Pat. No. 7,824,416.

(51) Int. Cl.
*A61B 17/22*    (2006.01)

(52) U.S. Cl.
CPC .............................. *A61B 17/22032* (2013.01)

(58) Field of Classification Search
CPC ............. A61B 17/22; A61B 17/22031; A61B 17/22032; A61B 17/221; A61B 17/2212; A61B 17/00867
USPC ................. 606/110, 113, 114, 127, 191–200; 604/103.06–103.09, 96.01
See application file for complete search history.

(56) References Cited

U.S. PATENT DOCUMENTS

| | | | |
|---|---|---|---|
| 3,464,322 A * | 9/1969 | Pequignot ........................... 92/91 |
| 4,762,130 A * | 8/1988 | Fogarty et al. ................ 606/159 |
| 4,834,724 A * | 5/1989 | Geiss et al. .................... 604/540 |
| 5,016,808 A * | 5/1991 | Heil et al. ...................... 228/176 |
| 5,054,501 A * | 10/1991 | Chuttani et al. ............... 600/585 |
| 5,226,888 A * | 7/1993 | Arney ....................... 604/103.07 |
| 5,236,437 A | 8/1993 | Wilk et al. |
| 5,295,959 A * | 3/1994 | Gurbel et al. ............. 604/103.13 |
| 5,437,638 A | 8/1995 | Bowman |
| 5,522,790 A | 6/1996 | Moll et al. |
| 5,524,633 A | 6/1996 | Heaven et al. |
| 5,540,659 A * | 7/1996 | Teirstein ........................ 604/104 |
| 5,554,119 A * | 9/1996 | Harrison et al. .......... 604/103.01 |
| 5,797,948 A * | 8/1998 | Dunham ........................ 606/194 |
| 5,814,064 A * | 9/1998 | Daniel et al. ................... 606/200 |
| 5,855,546 A * | 1/1999 | Hastings et al. ................... 600/3 |

(Continued)

FOREIGN PATENT DOCUMENTS

AT             352253         9/1979

OTHER PUBLICATIONS

Annex to Form PCT/ISA/206 dated Jan. 13, 2006, issued in corresponding International Application No. PCT/US2005/030769.

*Primary Examiner* — Dianne Dornbusch
(74) *Attorney, Agent, or Firm* — Bookoff McAndrews, PLLC (57) ABSTRACT

A medical retrieval device, and related method, for removing material, such as calculi, from a patient's body. In one embodiment, the device includes a handle, a sheath, and a retrieval assembly located at the distal end of the retrieval device. The retrieval assembly includes a plurality of legs, each of which includes a lumen for receiving fluid. The legs are made of an expandable material that will allow the legs to inflate when the lumen receives a fluid. In another embodiment, the device includes a core element wound to form a helical coil. The helical coil has a lumen for receiving a fluid. The core element is made of an expandable material that allows it to inflate when the lumen within the helical coil receives a fluid.

19 Claims, 7 Drawing Sheets

(56) References Cited

U.S. PATENT DOCUMENTS

| | | | |
|---|---|---|---|
| 5,957,963 A * | 9/1999 | Dobak, III | 607/104 |
| 6,030,362 A * | 2/2000 | Boussignac et al. | 604/101.01 |
| 6,261,312 B1 * | 7/2001 | Dobak et al. | 607/105 |
| 6,263,617 B1 | 7/2001 | Turcot et al. | |
| 6,283,940 B1 | 9/2001 | Mulholland | |
| 6,340,364 B2 * | 1/2002 | Kanesaka | 606/200 |
| 6,358,276 B1 * | 3/2002 | Edwin | 623/1.42 |
| 6,409,652 B1 * | 6/2002 | Kamdar et al. | 600/3 |
| 6,471,717 B1 * | 10/2002 | Dobak et al. | 607/105 |
| 6,482,226 B1 * | 11/2002 | Dobak, III | 607/104 |
| 6,527,781 B2 | 3/2003 | Bates et al. | |
| 6,533,804 B2 * | 3/2003 | Dobak et al. | 607/105 |
| 6,632,223 B1 * | 10/2003 | Keane | 606/41 |
| 6,685,722 B1 * | 2/2004 | Rosenbluth et al. | 606/200 |
| 6,711,444 B2 * | 3/2004 | Koblish | 607/122 |
| 6,740,096 B2 * | 5/2004 | Teague et al. | 606/127 |
| 6,923,808 B2 * | 8/2005 | Taimisto | 606/41 |
| 2002/0103519 A1 * | 8/2002 | Dobak et al. | 607/105 |
| 2003/0191492 A1 * | 10/2003 | Gellman et al. | 606/200 |
| 2006/0200171 A1 * | 9/2006 | Teague | 606/127 |

* cited by examiner

FIG. 9B

MEDICAL RETRIEVAL DEVICE

CROSS-REFERENCE TO RELATED APPLICATION

This application is a continuation of U.S. application Ser. No. 10/958,563, filed Oct. 6, 2004 (now U.S. Pat. No. 7,824,416), which is incorporated herein by reference in its entirety.

TECHNICAL FIELD

The invention generally relates to medical instruments such as retrieval devices for retrieving material from within a body. More particularly, the invention relates to retrieval devices having an adjustable retrieval assembly for capturing and releasing stones such as urinary tract stones, gall stones, and other biological materials.

BACKGROUND

Medical retrieval devices generally are used to retrieve biological and foreign material including stones from the body. Such medical retrieval devices may be used through an endoscope or a laparoscope.

One type of known medical retrieval device has a sheath and a retrieval assembly such as a basket that is movable in and out of the sheath. When the basket is within the sheath, the basket assumes a collapsed, reduced diameter profile. When the sheath is retracted relative to the basket or the basket is moved beyond the end of the sheath, the basket expands to a relatively larger diameter than when the basket is enclosed within the sheath.

With many known retrieval devices, materials are used in the retrieval assembly to enhance its rigidity. However, rigid materials used to enhance strength do so at the expense of flexibility. Moreover, rigid materials used in present retrieval assemblies have a fixed degree of flexibility and rigidity that cannot be altered to the conditions in which the retrieval assembly is used. The retrieval assembly must, on the one hand, be sufficiently strong to dilate the body tract and, on the other hand, be sufficiently flexible to negotiate body tracts having small diameters, tortuous pathways, and irregular lumens. Flexible retrieval assemblies can more easily capture large stones through the gaps in the legs of the retrieval assembly, than can rigid retrieval assemblies. When flexible materials are used in the retrieval assembly, however, rigidity and strength are compromised.

Also, in existing medical retrieval baskets, the contour of the baskets generally is round, oval, or pear-shaped, and the baskets are formed by a plurality of legs. Stones or other biological materials are captured in the basket by moving the basket around the material to be retrieved and maneuvering the material into the basket through the space between the basket legs.

After the material is captured in the basket, it is generally difficult to release the material from the basket if release of the captured material is required or indicated. The technical difficulty in releasing material such as a captured stone is a characteristic of known medical retrieval baskets in general. In some patients with long-standing clinical problems with urinary tract stones, a cicatrix may form in the tract as a result of trauma to its lining. The stenosis created by the cicatrix may not be so narrow so as to interfere with insertion of a retrieval basket while the basket is in a closed position. However, after the basket is expanded to capture the stone that is lodged beyond the stenotic area of the tract, the diameter of the basket containing the captured stone may exceed the diameter of the stenotic region of the urinary tract. Under these circumstances, release of the stone from the basket is a prerequisite for withdrawal of the device from the urinary tract. If the stone cannot be released, more invasive, surgical approaches are required to disengage the stone from the basket.

Improved devices and methods for retrieving material from a body are, therefore, needed.

SUMMARY OF THE INVENTION

It is an object of the invention to provide a medical retrieval device with variable flexibility and rigidity that gives an operator a variety of retrieval assembly configurations during a single clinical procedure. It is another object of the invention to provide a medical retrieval device that permits enhanced releasability of material captured by the device. It is yet another object of the invention to provide methods for using such devices to retrieve material from within a body. A common feature of the embodiments of the invention disclosed herein is a retrieval assembly that is inflatable upon introduction of a fluid.

In one aspect, the invention pertains to a device for retrieving material from a body. The device has a handle, a sheath, and a retrieval assembly. The sheath extends distally from the handle and has a proximal end, a distal end, and a lumen extending therethrough. The retrieval assembly is moveable relative to the sheath from an enclosed position in which the retrieval assembly is within the lumen of the sheath to an extended position in which the retrieval assembly is positioned beyond the distal end of the sheath. The retrieval assembly includes a proximal end, a distal end, a lumen and a plurality of legs. One or more of the plurality of legs has an axially disposed lumen for receiving a fluid. The lumen of one leg may be in fluid communication with the lumen of one or more of the other legs. The retrieval assembly has a first diameter and a second diameter. The second diameter is greater than the first diameter. The retrieval assembly achieves the second diameter when the fluid is introduced into the lumen of at least one leg.

Embodiments of this aspect of the invention can include the following features. For example, in one embodiment, an elongated member extending from the distal end of the handle is axially disposed within the lumen of the sheath and operably attached to the proximal end of the retrieval assembly. In one embodiment, the elongated member further includes a lumen that is in fluid communication with the lumen of at least one leg for introducing a fluid into the lumen of the at least one leg. The handle also can be adapted to couple to a pump, such as a syringe, to facilitate injection of the fluid. The fluid can be a gas, such as air, or a liquid, such as saline solution.

In one embodiment, the retrieval assembly is a basket formed from a single piece of material. The legs can be made from a polymeric material such as polyethylene terephthalate. One feature of the retrieval assembly includes basket legs joined at the distal end of the retrieval assembly, the proximal end of the retrieval assembly, or both. Further, the lumen of some or all of the basket legs can be in fluid communication with one another. In a particular embodiment, the lumen of all of the legs are in fluid communication at the proximal end of the retrieval assembly.

The device according to the invention features the ability to release captured material from the lumen of the retrieval assembly. In one embodiment, releasability of captured material is further enhanced by a balloon disposed within the lumen of the retrieval assembly. Specifically, the proximal end of the balloon is coupled to the proximal end of the basket while the distal end of the balloon is free within the lumen of the retrieval assembly. The balloon is expanded into the lumen of the retrieval assembly by inflating the balloon with an inflation fluid thereby displacing the captured material from the lumen of the retrieval assembly through the gaps between the legs of the retrieval assembly.

In another embodiment, the invention relates to a medical retrieval device having a retrieval assembly including a core element wound to form a helical coil. In one embodiment, the core element has a wall that defines a lumen extending longitudinally from the proximal end of the core element to the distal end of the core element. The proximal end of the core element is coupled to the distal end of an elongated member. The core element has a first diameter and a second diameter. The second diameter is greater than the first diameter, wherein the core element achieves the second diameter when a fluid is introduced into the lumen of the core element. In one embodiment, at least a portion of the wall extending throughout the core element is made of an inflatable material, such as a polymeric material. The helical coil has a plurality of turns and tapers in diameter from a larger diameter at the proximal end of the core element to a smaller diameter at the distal end of the core element. When a fluid is introduced into the lumen of the core element and the core element achieves the second diameter, adjacent turns of the helical coil contact and compress each other eliminating the gaps between the turns when the core element is of the first diameter.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

The invention generally relates to devices and methods for the retrieval of material, e.g., calculi, from the body of a patient. The devices and methods permit eased capture and release of material disposed or lodged in areas that are difficult to access in the body with minimal damage to the surrounding tissues. All of the following embodiments have at least one thing in common, an inflatable retrieval assembly with adjustable rigidity and flexibility controlled by regulating the amount of inflation pressure introduced into the retrieval assembly.

Figure 1A:
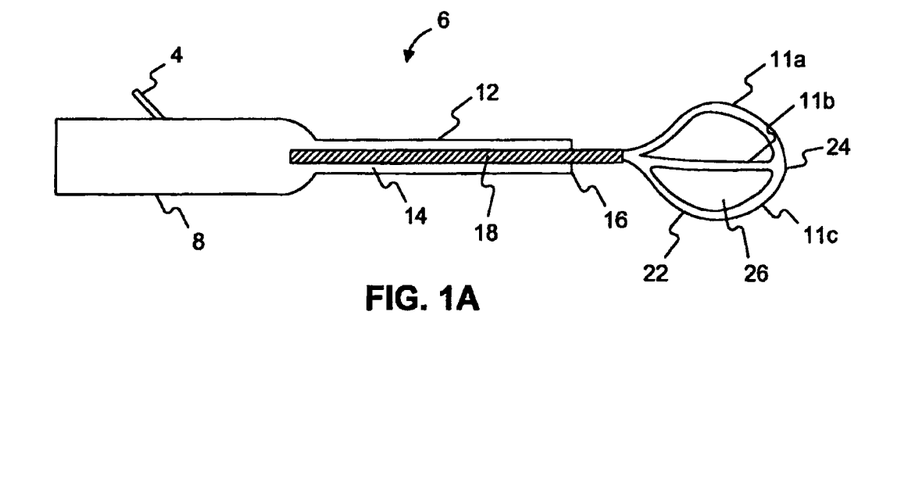
FIG. 1A is a plan view of a medical retrieval device including a retrieval assembly in an extended and expanded position according to an illustrative embodiment of the invention.

FIG. 1A is a plan view of a medical retrieval device including a retrieval assembly in an extended and expanded position according to an illustrative embodiment of the invention. The illustrative retrieval device 6 for removing material from a body includes a handle 8, a sheath 12, and a retrieval assembly 22 movable in a lumen 14 of the sheath 12. The handle 8, the sheath 12, and the retrieval assembly 22 illustrated in FIG. 1A are not shown in their correct size or proportion to each other. The sheath 12 is typically much longer than the handle 8 or the retrieval assembly 22 to allow insertion into a body cavity, canal, or tract. The size of the sheath 12 is dimensioned to fit the requirements of the application of the sheath 12 in the body. For example, for urological applications, the outside diameter of the sheath 12 can range from 1.7 Fr to 8.0 Fr. The sheath 12 has at least one lumen 14 therein, may be made from a single or more than one material, and extends from the handle 8 to a distal sheath end 16. The sheath 12 is preferably made of commonly available materials which provide sufficient strength and flexibility for adequate operation, but which are soft enough to avoid trauma or irritation to the tract or duct in which sheath 12 is deployed. Materials which may commonly be used to form sheath 12 include polyethylene, nylons, polyether block amide, polytetrafluoroethylene, urethanes, silicones, and other suitable polymer materials. The material used is preferably bio-compatible and inert to body fluids.

With continued reference to FIG. 1A, the retrieval assembly 22 (to be described in greater detail below) is in the extended position, i.e., the retrieval assembly 22 is extended beyond the distal end 16 of the sheath 12 and is no longer enclosed within the lumen 14 of the sheath 12. (As the term is used herein, proximal means closer to the operator and distal means away from the operator). The retrieval assembly 22 is, furthermore, in an expanded position, i.e., the retrieval assembly 22 and the lumen 26 of the retrieval assembly is expanded to its maximum diameter.

Figure 1B:
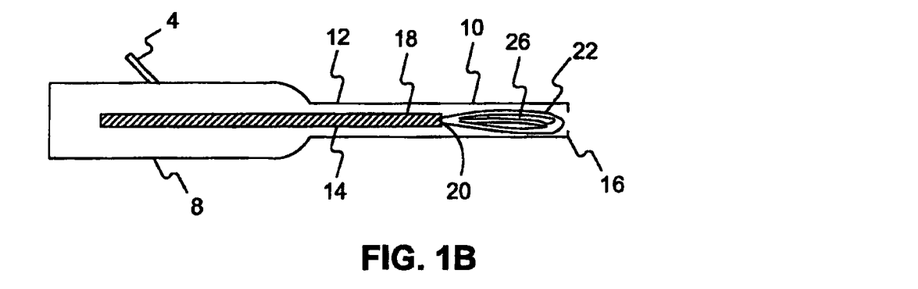
FIG. 1B is a plan view of the medical retrieval device illustrated in FIG. 1A including the retrieval assembly in an enclosed and collapsed position according to an illustrative embodiment of the invention.

FIG. 1B is a plan view of the medical retrieval device illustrated in FIG. 1A including the retrieval assembly in an enclosed and collapsed position according to an illustrative embodiment of the invention. The illustrative retrieval assembly is in the enclosed position, i.e., the retrieval assembly 22 is completely enclosed within the lumen 14 of the sheath 12 and it is proximal to the distal end 16 of the sheath 12. The retrieval assembly 22 is also in the collapsed position, i.e., the retrieval assembly 22 and the lumen 26 are collapsed such that the lumen 26 of the retrieval assembly 22 is substantially eliminated.

Figure 1C:
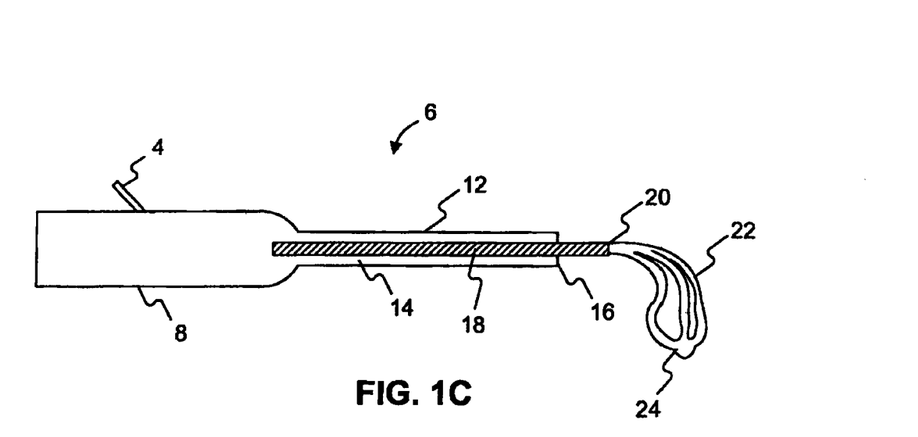
FIG. 1C is a plan view of the medical retrieval device illustrated in FIG. 1A including the retrieval assembly in an extended and collapsed position according to an illustrative embodiment of the invention.

FIG. 1C is a plan view of the medical retrieval device illustrated in FIG. 1A including the retrieval assembly in an extended, collapsed position according to an illustrative embodiment of the invention. The illustrative retrieval assembly 22 is in the extended position, i.e., the retrieval assembly 22 is extended beyond the distal end 16 of the sheath 12 and outside the lumen 14 of the sheath 12 (see, e.g., FIG. 1A). Furthermore, the retrieval assembly 22 is in the collapsed position, i.e., the retrieval assembly 22 and the lumen 26 of the retrieval assembly 22 are collapsed such that the lumen 26 of the retrieval assembly 22 is substantially eliminated (see, e.g., FIG. 1B).

Referring still to FIG. 1A, other features of the device 6 according to the invention include, for example, an elongated member 18 such as a cable, coil, shaft, guidewire or mandril wire that extends within the lumen 14 of the sheath 12 from at least one actuating mechanism 4 at the device handle 8 to the proximal end 20 of the retrieval assembly 22, where the elongated member 18 is attached to the proximal end 20 of the retrieval assembly 22. Operation of one or more actuating mechanism 4 by an operator causes the retrieval assembly 22 to move in and out of the lumen 14 of the sheath 12. Alternatively, the actuating mechanism 4 causes movement of the sheath 12 to advance the sheath 12 over the stationary retrieval assembly 22 and elongated member 18 combination, to thereby enclose the retrieval assembly 22 within the sheath 12, and the mechanism 4 can slide the moveable sheath 12 back to expose the stationary retrieval assembly 22. In general, both types of retrieval assembly/sheath movement are known, for example, in existing product designs available from Boston Scientific Corporation (Natick, Mass.).

Figure 2:
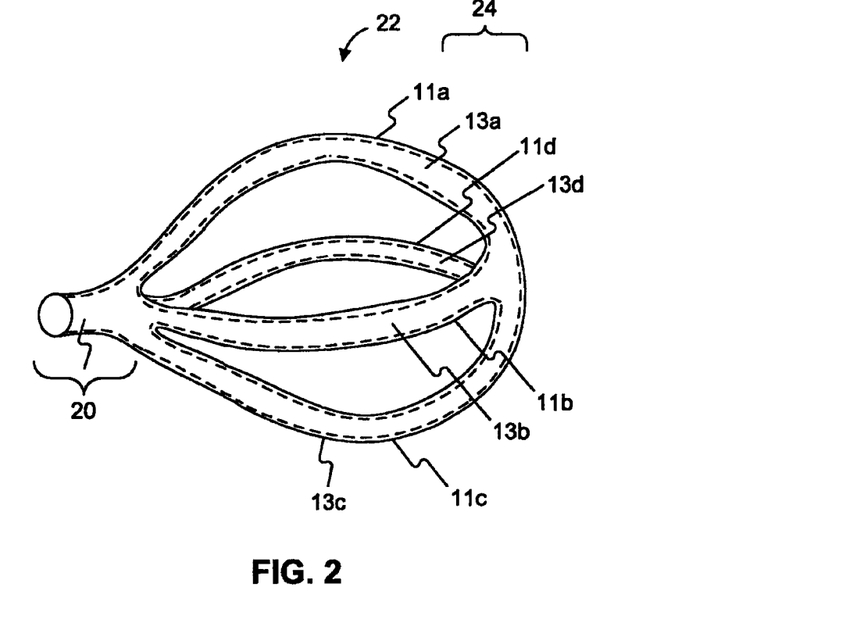
FIG. 2 is a plan view of a four-leg retrieval assembly including a plurality of inflatable legs having a lumen in communication with at least one other lumen of a leg according to an illustrative embodiment of the invention.

In general, referring to FIG. 2, the retrieval assembly 22 is similar to a basket formed by a plurality of legs 11. The number of legs 11 can be as many as 2-20, or more. In one embodiment of the invention, the retrieval assembly 22 is divisible into multiple basket portions such as a proximal basket portion 20 and a distal basket portion 24.

The legs 11 of the retrieval assembly 22 extend from the proximal end 20 to the distal end 24 of the retrieval assembly 22. One or more of the legs 11 of the retrieval assembly 22 have at least one lumen 13 axially disposed therein for inflating the legs 11. The legs 11 may be made of an expandable material, for example, a polymeric material, e.g., polyethylene, polyethylene terephthalate, silicone, polyurethane, or like material which can be formed as a "balloon" including a lumen 13 that may be filled or partially filled with an inflation fluid and from which the inflation fluid may be aspirated during a clinical procedure.

According to one embodiment of the invention, the basket legs can be constructed from a single piece of material. For example, the retrieval assembly 22 including the legs 11 are constructed using a "lost wax" process. For example, referring to FIG. 2, a wax-like material, such as glycerin or paraffin, for example, is used to form an inner, pre-mold of the retrieval assembly 22 in a specific configuration and size, e.g. a basket with three, four, or more legs 11. A polymeric material, such as polyethylene terephthalate, is molded over the glycerin or paraffin that forms the inner basket mold. Following cure of the polymeric outer wall, the glycerin or paraffin forming the inner basket mold is processed away, e.g., by melting, thereby forming the lumen 13 within the legs 11.

With continued reference to FIG. 2, in one embodiment, the lumen 13a of at least one basket leg 11a may be in fluid communication with the lumen 13c of at least one other leg 11c of the retrieval assembly 22. In a particular embodiment, the lumen 13 of at least one basket leg 11 is in fluid communication with the lumen of at least one other leg 11 at the proximal end 20 and the distal end 24 of the retrieval assembly 22. In an alternative embodiment, the lumens 13 of the inflatable basket legs 11 are not in fluid communication with one another. In yet another embodiment, the legs 11 may be in fluid communication at the distal end 24 of the retrieval assembly 22, but not at the proximal end 20 of the retrieval assembly 22, or alternatively, at the proximal end 20 but not at the distal end 24 of the retrieval assembly 22.

Figure 3:
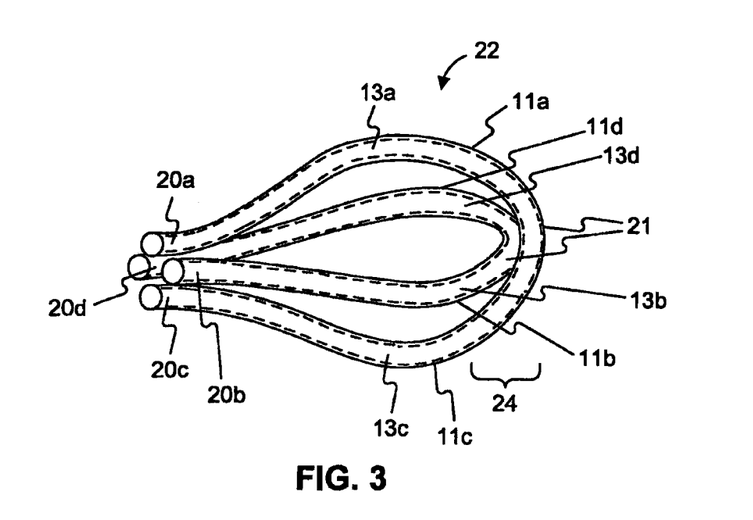
FIG. 3 is a plan view of a four-leg retrieval assembly including a plurality of inflatable legs having a lumen in communication with one other lumen of a leg according to an illustrative embodiment of the invention.

FIG. 3 is a plan view of another retrieval assembly including a plurality of inflatable legs having a lumen in communication with one other lumen of a leg according to an illustrative embodiment of the invention. The illustrative retrieval assembly has two basket legs 11a, 11c formed from a single hollow tube. As illustrated in FIG. 3, the tube is bent in two back along itself. The bend 21 is made at an intermediate point along the long axis of the tube to form two legs 11, for example, leg 11a and leg 11c, of the retrieval assembly 22 having lumens 13a, 13c, respectively. In one embodiment, the tubes forming the basket legs 11 are joined together at the distal end 24 of the retrieval assembly 22 at the bend 21 in the tubes by an adhesive, or by a heat-shrink sleeve, for example.

Figure 4:
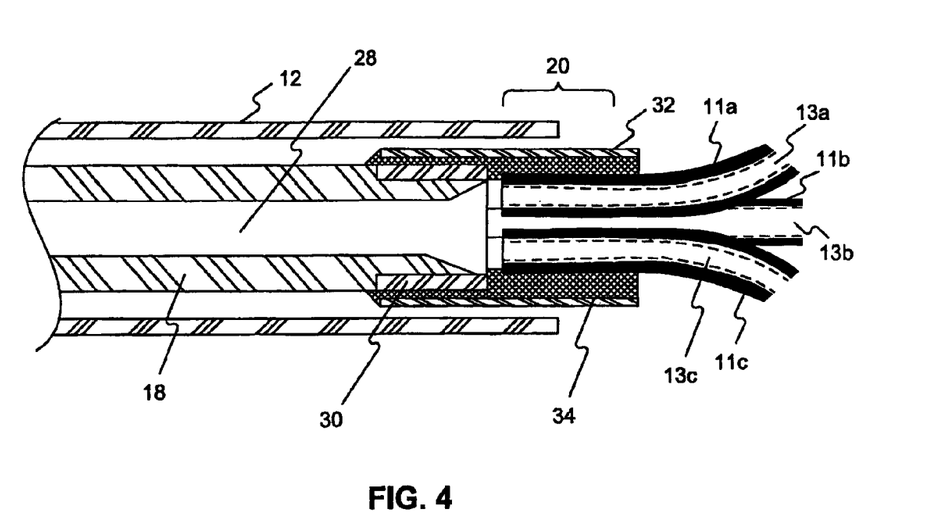
FIG. 4 is an expanded view of a portion of a medical retrieval device according to an illustrative embodiment of the invention.

FIG. 4 is an expanded view of a portion of a medical retrieval device according to an illustrative embodiment of the invention. Referring to FIG. 4, in one embodiment of the invention, the elongated member 18 includes a lumen 28 axially disposed therethrough. The lumen 28 of the elongated member 18 is in fluid communication with the lumen 13 of at least one leg 11. The lumen 28 of the elongated member 18 provides a channel for introducing an inflation fluid into the lumen 13 of at least one basket leg 11. The inflation fluid can be a gas, such as air, for example, or a liquid such as saline solution, for example.

With continued reference to FIG. 4, the illustrative retrieval assembly 22 is connected to the distal end 26 of the elongated member 18 by a swaged ring 30. A connecting cannula 32 overlays the swaged ring 30 and the proximal end 20 of the retrieval assembly 22 and is crimped or glued to the swaged ring 30 to connect the retrieval assembly 22 to the elongated member 18. Additionally, a sealant or adhesive 34 may be used to fill the gap between the connecting cannula 32 and the proximal end 20 of the retrieval assembly 22 to prevent leakage of the inflation fluid from the lumen 28 of the elongated member 18. An inlet for introducing the inflation fluid may be located anywhere along the device 6, for example, in the handle 8 (not shown).

Figure 5:
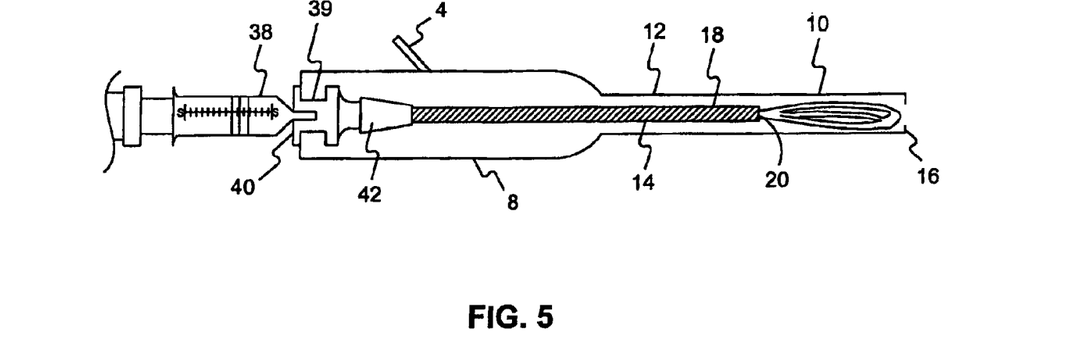
FIG. 5 is a plan view of a medical retrieval device with a syringe coupled to its proximal end according to an illustrative embodiment of the invention.

FIG. 5 is a plan view of a medical retrieval device including a syringe coupled to the handle according an illustrative embodiment of the invention. Referring to FIG. 5, the proximal end 3 of the illustrative handle 8 includes a coupling 39 adapted to couple to the tip of a syringe 38. The coupling 39 of the handle 8 includes a fluid injection inlet port 40. In one embodiment, the coupling 39 includes a luer fitting 42 connecting the syringe 38 to a standard handle system 8 found in existing handle designs available from, for example, Boston Scientific Corporation (Natick, Mass.).

Figure 6A:
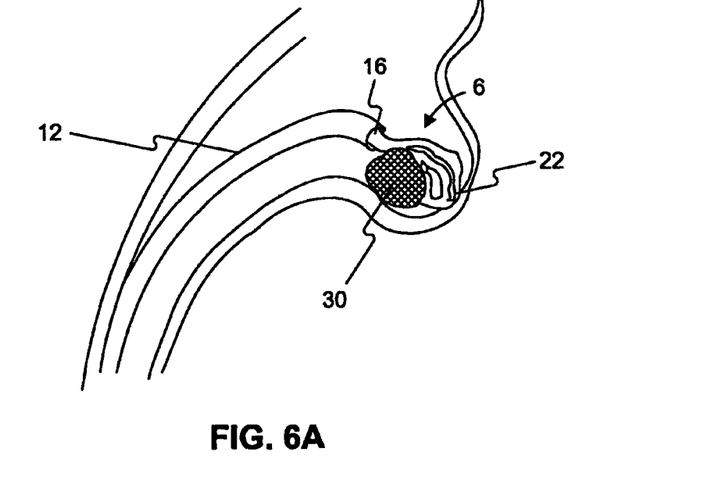
FIGS. 6A-6B are diagrammatic representations of a clinical application of the device illustrated in FIGS. 1A-1C.
Figure 6B:
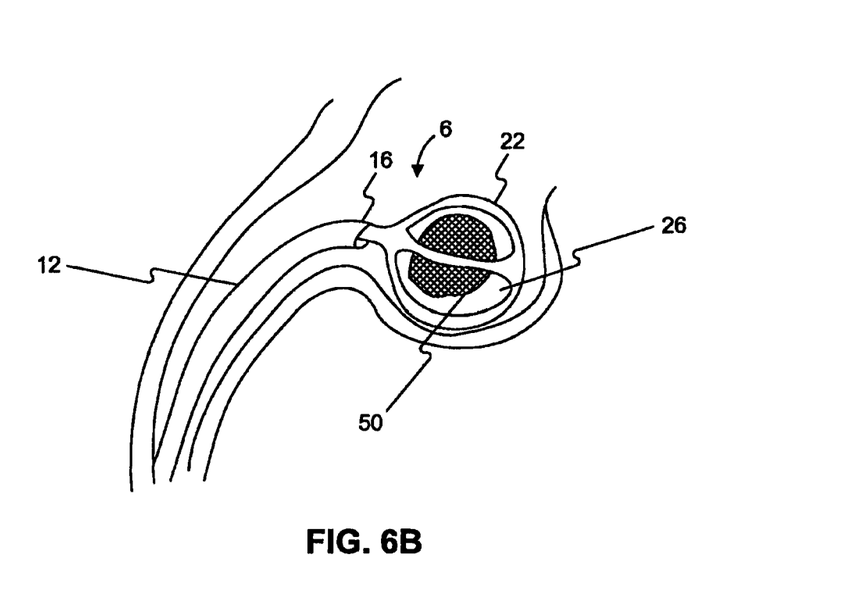

In another aspect, the invention relates to a method for capturing and/or releasing material in a body tract with the medical retrieval device described herein. FIGS. 6A-6B are diagrammatic representations of a clinical application of the device according to an illustrative embodiment of the invention. For example, the method for retrieving material from a body tract according to the invention includes inserting the device 6 into the body of a patient by an operator to an anatomical site where the material to be retrieved is located (e.g., a stone in the ureter). The operator inserts the retrieval assembly 22 into the body (not shown) while the retrieval assembly is in a collapsed, enclosed position and has a relatively small first diameter that allows the retrieval assembly 22 to be enclosed within the lumen 14 of the sheath 12. Referring to FIG. 6A, while the basket legs 11 are deflated, the operator extends the retrieval assembly 22 from the distal end 16 of the sheath 22 into the extended, collapsed position (also see, e.g., FIG. 1C). Once the retrieval assembly 22 is positioned near the material to be retrieved, e.g. a stone 50, an inflation fluid is injected into one or more of the lumens 13 of the basket legs 11, causing the legs 11 of the retrieval assembly 22 to expand such that the retrieval assembly achieves a second diameter larger than the first diameter and assumes an expanded, extended position illustrated in FIG. 6B (see also, e.g., FIG. 1A). Referring to FIG. 6B, the operator manipulates the retrieval assembly 22 around the material 50 to entrap or capture material 50 within the lumen 26 of the retrieval assembly 22. The material 50 includes any biological or foreign material, for example, a kidney stone, a ureteral stone, a urethral stone, a urinary bladder stone, a gallbladder stone, or a stone in the biliary tree.

Figure 7A:
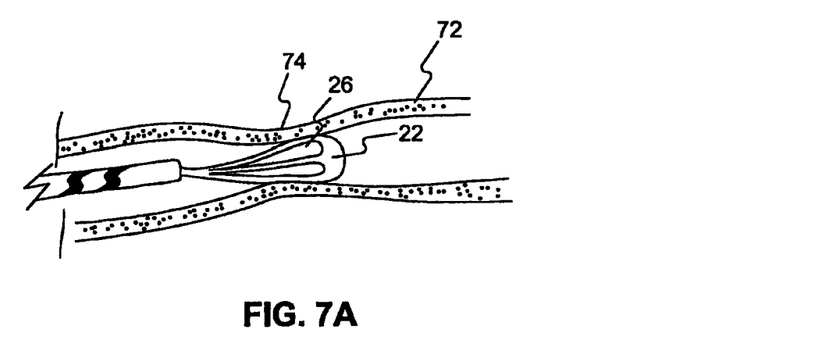
FIGS. 7A-7B are diagrammatic representations of another clinical application of the device illustrated in FIGS. 1A-1C.
Figure 7B:
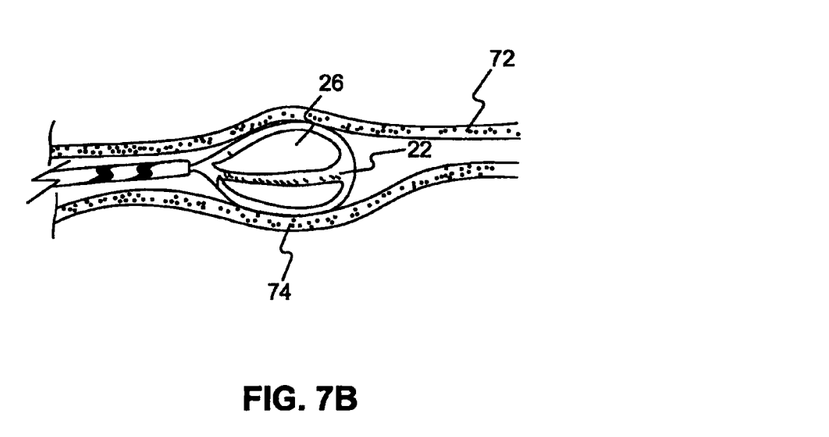

FIGS. 7A-7B depict a diagrammatic representation of another clinical application of the device according to the invention. The rigidity of the retrieval assembly 22 is adjustable by regulating the amount of inflation fluid injected into or aspirated from the lumen 13 of the basket leg 11. This feature is a significant advantage of the present invention over the prior art because the diameter and flexibility of the retrieval assembly is adjustable during a single procedure. For example, referring to FIG. 7A, the device 6 according to the invention may be used to remove a restriction 74 in a body canal. With the retrieval assembly positioned at the restriction 74, the operator expands the retrieval assembly 22 to dilate the restriction 74 as shown in FIG. 7B by injecting greater volumes of an inflation fluid into the lumen 13 of at least one leg 11 of the retrieval assembly 22. As the retrieval assembly 22 expands, the restriction 74 is dilated.

Figure 8A:
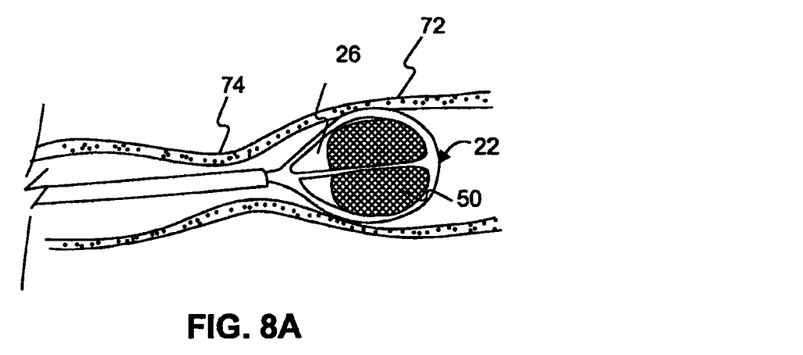
FIGS. 8A-8B are diagrammatic representations of yet another clinical application of the device illustrated in FIGS. 1A-1C including the release of a captured stone.
Figure 8B:
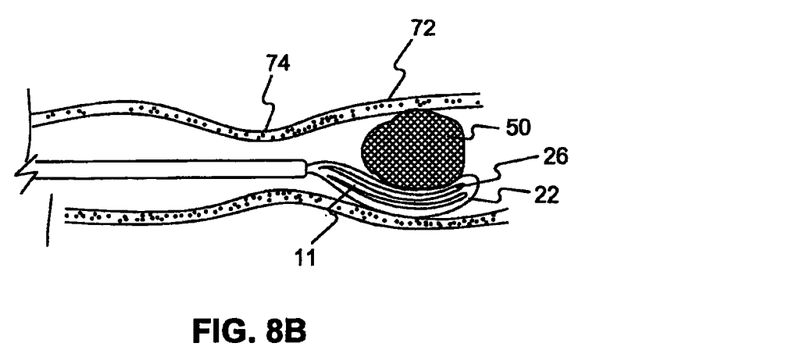

FIGS. 8A-8B are diagrammatic representations of yet another clinical application of the device of the invention. For example, during a procedure to retrieve a material 50, if the need arises, the captured material 50 may be released from the retrieval assembly 22. This additional feature may be useful when an impassable stricture is encountered in the body tract. Referring to FIG. 8A, for example, if the outside diameter of the expanded retrieval assembly 22 with the material 50 captured within its lumen 26 is larger than the internal diameter of a restriction 74 in the body tract 72 in which the material 50 is located, the retrieval assembly 22 can be deflated by aspirating a portion or all of the inflation fluid from the retrieval assembly 22, as illustrated in FIG. 8B, to release captured material 50 from the lumen 26 with minimal trauma to the surrounding tissues in the body tract 72.

Figure 8C:
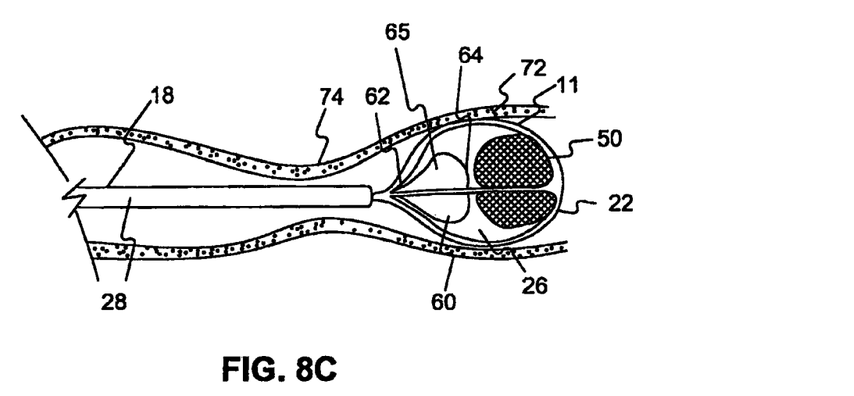
FIG. 8C is a partial view of a medical retrieval device with an inflatable balloon partially extended within the lumen of the retrieval assembly according to an illustrative embodiment of the invention.

FIG. 8C is a partial view of a medical retrieval device with an inflatable balloon partially expanded within the lumen of the retrieval assembly according to an illustrative embodiment of the invention. The illustrative retrieval assembly 22 includes a balloon 60 disposed within the lumen 26 of the retrieval assembly 22. If the need arises during a procedure to release the captured material 50 from the lumen 26 of the retrieval assembly 22, the balloon 60 is inflated within the lumen 26 of the retrieval assembly 22 until the balloon 60 abuts the stone 50. The balloon 60 is inflated further into the lumen 26 of the retrieval assembly 22 until the stone 50 is pushed out of the retrieval assembly lumen 26 through the gaps between the retrieval assembly legs 11. Other retrieval devices, such as a retrieval assembly with conventional wire legs (not shown), can also incorporate a similar balloon to enhance releasability of captured material.

With the continued reference to FIG. 8C, the balloon 60 typically has a fixed proximal end 62 and a fee distal end 64. The lumen 65 of the balloon 60 is in fluid communication with an inflation port (not shown) or the lumen 28 of the elongated member 18. Inflation fluid may be introduced and aspirated from the balloon 60 via the inflation port or elongated member 18.

Figure 9A:
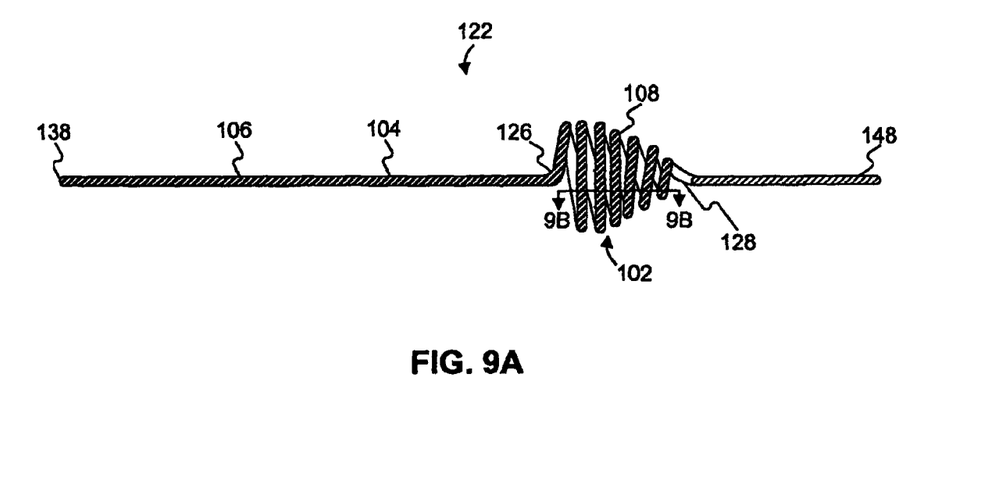
FIG. 9A is a plan view of a portion of a medical retrieval device including a retrieval assembly according to an illustrative alternative embodiment of the invention.

FIG. 9A is a plan view of a medical retrieval device including a retrieval assembly according to another illustrative embodiment of the invention. The illustrative retrieval assembly 122 includes a core element 102, wound to form a helical coil 108 and, optionally, an elongated member 104 that extends substantially longitudinally proximal to the helical coil 108 and is coupled to the proximal end 126 of the core element 102. A wall 106 of the core element 102 defines a lumen 120 that extends longitudinally from at least a portion of the elongated member 104 to and through at least a portion of the helical coil 108. In a particular embodiment according to the invention, the lumen 120 extends throughout the length of the elongated member 104 and through the length of the core element 102.

With continued reference to FIG. 9A, the overall length of the illustrative retrieval assembly depends on the application for which the retrieval assembly 122 is intended. Generally the overall length from the proximal end 138 to the distal end 148 is in the range of about 50 cm to about 250 cm. For urinary applications, the total length of the retrieval assembly 22 is preferably about 140-220 cm, and most preferably about 200 cm. Other applications in the body will require retrieval assemblies of different lengths. The maximum diameter of the core element 102 is typically in the range of about 0.04 cm to 0.10 cm, and preferably about 0.05 cm. The number of turns, the maximum diameter, and the length of the tapered helical coil 108 depends, again, on the intended use of the retrieval assembly 22. Typically, the helical coil 108 has between about 5 and 15 turns, and preferably about 7 to 10 turns. Its maximum diameter, at the proximal end 126 of the helical coil 108 is in the range of about 0.2 cm to 3.0 cm, and for usual applications is about 0.5-1.5 cm, and most preferably is about 0.7-0.8 cm. The overall length of the helical coil 108 typically is in the range of about 0.5 cm to about 3.0 cm, and for most applications is preferably about 1.5 cm. As illustrated in FIG. 9A, the helical coil 108 tapers in diameter from a larger diameter at the proximal end 126 of the core element 102 to a smaller diameter at the distal end 128 of the core element 102. In an alternative embodiment, the helical coil 108 includes a larger diameter at the distal end and a smaller diameter at the proximal end (not shown). It will be appreciated that FIG. 9A is not to scale; the overall length of the device is over one hundred times its maximum diameter, for example.

Figure 9B:
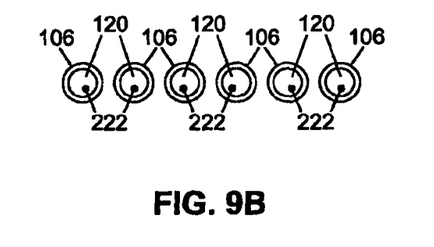
FIG. 9B is a cross-sectional view of the retrieval assembly illustrated in FIG. 9A taken at 9B-9B.

FIG. 9B is a cross-sectional view of the helical coil 108 portion of the retrieval assembly 122 in FIG. 9A. At least a portion of the wall 106 of the core element 102 is made of an inflatable material, e.g., a polymeric material. In one embodiment, the elongated member 104 and the core element 102 are made of polyethylene, polyethylene terephthalate, silicone, polyurethane, or like material which can be inflated by introducing an inflation fluid, as described above, into the lumen 106 of the retrieval assembly during intended clinical procedures. The retrieval assembly 122 may feature a core wire 222 that extends throughout the length of the retrieval assembly 122. The inflatable material, e.g. polyethylene terephthalate, is attached to the core wire 122 by gluing or other means known in the art.

Other features of the retrieval assembly according to the invention include a handle (not shown) secured to the proximal end of the elongated member 104. The handle may be adapted to couple to a syringe, (see, e.g., FIG. 5) allowing introduction of an inflation fluid into the lumen 104 of at least the core element 102. Upon introduction of the inflation fluid, at least the helical coil 108 will adopt a larger diameter and adjacent turns of the coil may abut each other due to the inflated state of the helical coil 108.

In use, device 106 is inserted in its deflated state into an anatomical lumen, such as a ureteral passage, to retrieve biological or foreign materials obstructing the lumen. When device 106 is in the deflated state, the core element 102 is of a first diameter with small gaps, up to about 2 mm wide, between the adjacent turns forming the tapered helical coil 108. The small gaps allow small stones or fragments thereof to enter the lumen of the helical coil 108. Upon introduction of an inflation fluid, the core element 102 is inflated and adopts a second diameter that is greater than the first diameter. As the helical coil 108 expands, adjacent turns of the helical coil 108 expand into the gaps between the turns minimizing the size of the gaps. In the inflated configuration, the retrieval assembly 122 is more effective in capturing and immobilizing small fragments which are removed from the body tract by withdrawing the retrieval assembly 122 from the body tract. If the need arises to release the captured stone, the helical coil 108 is deflated and the stone is released between the gaps of the turns.

Variations, modifications, and other implementations of what is described herein will occur to those of ordinary skill in the art without departing from the spirit and the scope of the invention. The invention is not to be defined only by the preceding illustrative description.

What is claimed is:

1. A medical retrieval device, comprising:
   a core element defining a lumen extending longitudinally therethrough, a portion of the core element forming a tapering helical coil, the coil comprising a plurality of turns and a cross-section having a first diameter and a second diameter, wherein the second diameter is greater than the first diameter, and wherein, upon introduction of a fluid into the lumen, the coil is configured to inflate due to fluid pressure applied to an interior surface of the lumen to the second diameter to form a stone capturing configuration; and
   an interior space formed radially within and by the coil, the interior space forming a cavity that is free of any other portion of the device.

2. The device of claim 1, further comprising a core wire extending within the lumen.

3. The device of claim 1, wherein the helical coil tapers from a larger diameter at a proximal end of the helical coil to a smaller diameter at a distal end of the helical coil.

4. The device of claim 1, wherein the core element consists of the single lumen.

5. The device of claim 1, wherein the second diameter at a proximal end of tapering helical coil is configured to be small enough so that the core element is moveable relative to a body lumen.

6. A retrieval assembly, comprising:
   a core element defining a lumen extending longitudinally from a proximal end of the core element to a distal end of the core element,
   wherein a portion of the core element forms a helical coil, the helical coil having a proximal end and a distal end, a cone shape extending from the proximal end to the distal end, and a plurality of turns, and
   wherein, in a first configuration of the core element, adjacent turns of the coil are separated by a first distance, and in a second configuration of the core element, adjacent turns of the coil are separated by a second distance due to expansion of the core element, the first distance being larger than the second distance, and wherein, in a third configuration, adjacent turns of the coil abut against each other.

7. The retrieval assembly of claim 6, wherein the core element is inflated by introducing a fluid into the lumen of the core element.

8. The retrieval assembly of claim 7, wherein the second configuration and the third configuration of the core element are achieved by expanding the core element.

9. The retrieval assembly of claim 6, further comprising a core wire extending within the lumen.

10. The retrieval assembly of claim 9, wherein the core wire is attached to the core element.

11. The retrieval assembly of claim 6, wherein the helical coil tapers in diameter from a larger diameter at a proximal end of the coil to a smaller diameter at a distal end of the coil.

12. The retrieval assembly of claim 6, wherein a portion of the core element distal the coil is substantially straight.

13. The retrieval assembly of claim 6, further comprising an elongate member coupled to the proximal end of the core element.

14. The retrieval assembly of claim 13, wherein the lumen further extends throughout a length of the elongate member.

15. A medical retrieval device, comprising:
   a core element defining a lumen extending longitudinally therethrough, a portion of the core element forming a tapering helical coil, the coil comprising
   a plurality of turns,
   an interior space formed radially within the coil, the interior space forming a hollow cavity that is free of any other portion of the device, and
   a cross-section having a first diameter and a second diameter, wherein the second diameter is greater than the first diameter, and wherein, upon introduction of a fluid into the lumen, the coil is configured to expand to the second diameter and the second diameter at a proximal end of the coil is about 0.2 cm to 3.0 cm.

16. The device of claim 15, wherein said expansion to the second diameter includes inflating the coil by the introduction of the fluid into the lumen.

17. The device of claim 15, wherein the core element consists of the single lumen.

18. The device of claim 15, wherein the second diameter at a proximal end of the coil is about 0.5 cm to 1.5 cm.

19. The device of claim 15, wherein the second diameter at a proximal end of tapering helical coil is configured to be small enough so that the core element is moveable relative to a body lumen.

* * * * *